United States Patent [19]

Kastner et al.

[11] 4,342,829

[45] Aug. 3, 1982

[54] PROCESS FOR PREPARING NARASIN

[75] Inventors: Ralph E. Kastner, Indianapolis; Robert L. Hamil, Greenwood, both of Ind.

[73] Assignee: Eli Lilly and Company, Indianapolis, Ind.

[21] Appl. No.: 261,068

[22] Filed: May 6, 1981

[51] Int. Cl.³ .................... C12P 17/16; C12N 1/20; C12R 1/465
[52] U.S. Cl. .................................. 435/118; 435/253; 435/886
[58] Field of Search .................... 435/118, 253, 886

[56] References Cited

U.S. PATENT DOCUMENTS 4,038,384 7/1977 Berg et al. .......................... 424/122

OTHER PUBLICATIONS

Berg et al., Journal of Antibiotics, 31 1-6 (1978).
Boeck et al., Development in Industrial Microbiology, 18, 471-485 (1977).

*Primary Examiner*—Lionel M. Shapiro
*Attorney, Agent, or Firm*—Dwight E. Morrison; Arthur R. Whale

[57] ABSTRACT

The new microorganism *Streptomyces granuloruber*, NRRL 12389 and the fermentation process for preparing narasin by submerged aerobic fermentation of this organism.

4 Claims, No Drawings

PROCESS FOR PREPARING NARASIN

BACKGROUND OF THE INVENTION

This invention relates to a new microbiological process for preparation of the antibiotic narasin.

Narasin is a known polyether antibiotic. Production of narasin by fermentation of *Streptomyces aureofaciens* NRRL 5758 or *Streptomyces aureofaciens* NRRL 8092, has been described by Berg et al., U.S. Pat. No. 4,038,384 (July 26, 1977). See also Berg et al. in *J. Antibiot.* 31, 1–6 (1978).

Boeck et al. describe "Narasin, A New Polyether Antibiotic: Discovery and Fermentation Studies", Chapter 38, Pages 471–485, Volume 18, *Developments In Industrial Microbiology* [A Publication of the Society for Industrial Microbiology (1977)].

Narasin is active against gram-positive bacteria, anaerobic bacteria, and fungi, and is useful as an anticoccidial agent and as an agent for increasing feed-utilization in ruminants.

SUMMARY OF THE INVENTION

The present invention relates to a new process for the preparation of the antibiotic narasin by cultivating a newly discovered strain designated herein as *Streptomyces granuloruber*, NRRL 12389, or a narasin-producing mutant or variant thereof, in a culture medium containing assimilable sources of carbon, nitrogen, and inorganic salts under submerged aerobic fermentation conditions until a substantial amount of narasin is produced by said organism in said culture medium and, optionally, isolating said narasin from the culture medium.

This invention further relates to the biologically pure culture of the microorganism *Streptomyces granuloruber*, NRRL 12389, which is useful for the production of narasin.

DETAILED DESCRIPTION

The new microorganism of this invention is a biologically pure culture derived from a soil sample collected near the Surinam River, Surinam, South America. The culture was given the number A-39912 for identification purposes.

Culture A-39912 is classified as *Streptomyces granuloruber*, based upon a simultaneous culturing of *Streptomyces rubra*; *Streptomyces griseoruber*; and *Streptomyces griseoaurantiacus*, using the methods and media recommended by Shirling and Gottlieb ["Methods of Characterization of Streptomyces species," *Int. Bull. of Systematic Bacteriol.* 16, 313–340 (1966)], along with certain supplementary tests. Culture A-39912 was also compared with the description of *Streptomyces longispororuber* reported by Gerber, *J. Antibiot.* 28, 194–199 (1975).

Culture A-39912 differs from *Streptomyces rubra* by producing granules, that is, crystals of undecylprodiginine, a purplish-red dye, by producing a purplish-red to black vegetative mycelium, and by reducing nitrate. Culture A-39912 produces a red and gray aerial mycelium in contrast to the gray aerial mycelium of *Streptomyces griseoruber*. The purplish-red to black vegetative mycelium produced by culture A-39912 also differs from the yellow brown to reddish orange vegetative mycelium of *Streptomyces griseoruber*. *Streptomyces griseoaurantiacus* does not produce the distinctive purplish-red to black vegetative mycelium, as does culture A-39912. Neither *Streptomyces griseoruber* nor *Streptomyces griseoaurantiacus* produces the purplish-red crystals of undecylprodiginine as does A-39912.

Thus, comparison of culture A-39912 with the above-named cultures shows significant differences. Our culture is considered to be a new species and is described as *Streptomyces granuloruber*.

CHARACTERIZATION OF NARASIN-PRODUCING STRAIN

Morphology

Produces spiralled sporophores. The spores are smooth as determined by electron microscopy and are oval to slightly cylindrical in shape. The spores measure an average of 1.3 $\mu m \times 2.015$ $\mu m$ with a range of 1.3 $\mu m \times 1.3$ $\mu m$ to 2.6 $\mu m$.

Cultural Characteristics

The growth characteristics of *Streptomyces granuloruber* on various media are presented in the following Table I.

Color names were assigned according to the ISCC-NBS method (K. L. Kelly and D. B. Judd, "The ISCC-NBS Methods of Designating Colors and a Dictionary of Color Names," U.S. Department of Commerce Circ. 553, 1955, Washington, D.C.). Figures in parentheses refer to the Tresner and Backus color series [H. D. Tresner and E. J. Backus, "System of Color Wheels for Streptomycete Taxonomy," *Appl. Microbiol.* 11, 335–338 (1956)]. Color tab designations are underlined. The Maerz and Paul color blocks [A. Maerz and M. R. Paul, "Dictionary of Color," McGraw-Hill Book Co., Inc., New York, N.Y., (1950)] are enclosed in brackets.

TABLE I

| Medium | Cultural Characteristics on Various Media — Characteristics |
| --- | --- |
| Tomato paste oatmeal agar | Abundant growth, reverse purplish black [56E8]; fair aerial mycelium and spores (GY) 5fe light grayish brown reddish to (R) 5dc grayish yellowish pink. None or slight brown water-soluble pigment. |
| Glycerol-glycine agar | Abundant growth, reverse dark purplish red [55H4]; fair aerial mycelium and spores (R) 5dc grayish yellowish pink. No soluble pigment. |
| Yeast extract-malt extract agar (ISP medium #2) | Abundant growth, reverse black to blackish red [56C1] to [56H12]. Abundant aerial mycelium and spores (W) b white to (GY) d light gray; none or slight brown water soluble pigment. |
| Oatmeal agar (ISP medium #3) | Abundant growth, reverse medium reddish brown [7J7]; good aerial mycelium and spores (GY) d light gray; slight brown water-soluble pigment. |
| Inorganic salts - starch agar (ISP medium #4) | Abundant growth, reverse moderate reddish brown [7J9]; abundant aerial mycelium and spores (R) 5dc grayish yellowish pink; no water-soluble pigment. |
| Glycerol asparagine agar (ISP medium #5) | Abundant growth, reverse medium reddish brown [6G9]; good aerial mycelium and spores (R) 5dc grayish yellowish pink. No |

TABLE I-continued

Cultural Characteristics on Various Media

| Medium | Characteristics |
|---|---|
| | water-soluble pigment. |
| Nutrient agar | Fair growth, reverse grayish yellow [12B2]; no aerial mycelium or spores, no color assigment; no water-soluble pigment. |
| Tryptone yeast extract agar | Fair growth, reverse grayish yellow [12B2]; no aerial mycelium or spores, no color assigment; no water-soluble pigment. |
| Calcium malate agar | Fair growth, reverse pale yellow [10B2]. Fair aerial mycelium and spores (GY) 2ge light olive brown. No water-soluble pigment. |
| Emerson's agar | Abundant growth, reverse moderate yellow brown [13H7]. No aerial mycelium or spores, no color assigment. No water-soluble pigment. |
| Glucose asparagine agar | Good to abundant growth, reverse blackish red [56J10]; good to abundant aerial mycelium and spores (GY) 5fe light grayish reddish brown. Slight brown water-soluble pigment. |
| Bennett's agar | Good growth, reverse grayish yellow [12J5]; no aerial mycelium or spores, no color assigment; no water-soluble pigment. |
| Tyrosine agar | Abundant growth, reverse dark purplish red [54J6]; fair to good aerial mycelium and spores (W) b white to (R) 6ec grayish yellowish pink. Brownish water-soluble pigment. |
| Czapek's solution agar | Fair growth, reverse pale orange yellow [9B2]; fair aerial mycelium and spores (GY) 2dc yellowish gray. Slight brown water-soluble pigment. |

The organism was studied for selected physiological properties in accordance with standard procedures. The properties observed and characteristics found are recorded in Table II:

TABLE II
PHYSIOLOGICAL PROPERTIES OF A-39912
Melanoid-like Pigment Production on:

| | |
|---|---|
| 1. Tryptone yeast extract broth (ISP #1) | No melanoid-like pigment |
| 2. Peptone yeast extract iron slants (ISP #6) | No melanoid-like pigment |
| 3. Tyrosine agar slants (ISP #7) | No melanoid-like pigment |
| Nitrate Reduction | Positive reaction |
| Gelatin Liquefaction | Positive reaction - 100% at 14 days |
| Potato Plug | No growth |
| Carrot Plug | No growth |
| Starch Hydrolysis Use ISP med. #4 (Inorganic Salts-Starch) | Hydrolyzed |
| Temperature Requirements | Abundant growth and sporulation from 25° C. to 43° C. No growth at <25° C. or >43° C. |
| Skim Milk | Peptonized |
| NaCl Tolerance | ≧3.5% but <4.0% |
| pH range for growth | Growth from pH 5.5 to |

TABLE II-continued
PHYSIOLOGICAL PROPERTIES OF A-39912
Melanoid-like Pigment Production on:

pH 9.5

Carbon utilization was determined using Pridham and Gottlieb's basal medium to which the carbon sources were added at a final concentration of 1.0%, according to the teaching of Shirling and Gottlieb, supra. The carbon sources were sterilized before being added to the basal medium. Plates were read after eight and fourteen days incubation at 30° C., the final readings being reported.

The results of the carbon utilization tests carried out with culture A-39912 are set forth in Table III.

TABLE III
CARBON UTILIZATION

| Substrate: Carbon Sources Added to Pridham and Gottlieb's Basal Medium | Reaction of A-39912 at 14 Days |
|---|---|
| L-Arabinose | ++ |
| D-Fructose | ++ |
| D-Glucose | ++ |
| i-Inositol | ++ |
| D-Mannitol | − |
| D-Raffinose | + |
| L-Rhamnose | ++ |
| Sucrose | ± |
| D-Xylose | ++ |
| D-Galactose | ++ |
| Control - Carbon | − |

*Carbon Sources of the International Streptomyces Project (Shirling and Gottlieb, supra.)
Key:
++ = Strong positive utilization
+ = Positive utilization
± = Doubtful utilization
− = Negative utilization

Cell Wall Studies

Using hydrolyzed whole cells of the organism, the presence of certain diagnostic sugars were determined. Isolated cell walls were used to determine the isomers of diaminopimelic acid.

The cell-wall sugars were determined using a modification of the procedure of M. P. Lechavalier ["Chemical Methods as Criteria for the Separation of Actinomycetes Into Genera." These methods were developed at workshops sponsored by the Subcommittee on Actinomycetes of the American Society of Microbiology, (Dr. Thomas G. Pridham, Convenor), and held at the Institute of Microbiology, Rutgers University, The State University of New Jersey, New Brunswick, N.J., (1971)]. The isomers of diaminopimelic acid were determined using the method of Becker et al., Appl. *Microbiol.* 11, 421–423 (1964). All plates were read after 8 to 14 days at 30° C. The results of these cell-wall studies are set forth below.

| Test | Result Observed |
|---|---|
| Isomers of 2,6-diaminopimelic acid | LL-isomer |
| Diagnostic sugars detected | Glucose, Ribose |

A comparison of the carbon utilization patterns of strain A-39912, *Streptomyces (chainia) rubra* ATCC 17755, *Streptomyces griseoruber* ATCC 23919, and *Strep-* tomyces griseoaurantiacus ATCC 19840 is set forth in Table IV, which follows.

TABLE IV

CARBON UTILIZATION PATTERNS OF A-39912, STREPTOMYCES (CHAINIA) RUBRA ATCC 17755, STREPTOMYCES GRISEORUBER ATCC 23919, AND STREPTOMYCES GRISEOAURANTIACUS ATCC 19840

| Carbon Source | A-39912 | ATCC 17755 | ATCC 23919 | ATCC 19840 |
|---|---|---|---|---|
| D-Glucose | ++ | ++ | ++ | ++ |
| L-Arabinose | + | − | ++ | ++ |
| Sucrose | ± | + | − | − |
| S-Xylose | ++ | + | ++ | ++ |
| Inositol | ++ | ± | ++ | ++ |
| D-Fructose | ++ | + | ++ | ++ |
| D-Mannitol | − | + | − | ++ |
| Rhamnose | ++ | + | ++ | ++ |
| Raffinose | ± | ± | − | − |

++ = Strong positive utilization
+ = Positive utiliztion
± = Doubtful utilization
− = Negative utilization A comparison of the similarities and differences between A-39912 and Streptomyces (chainia) rubra ATCC 17755, Streptomyces griseoruber ATCC 23919, and Streptomyces griseoaurantiacus ATCC 19840 is outlined in Table V.

TABLE V

Comparison of A-39912, Streptomyces (chainia) rubra ATCC 17755, Streptomyces griseoruber ATCC 23919, and Streptomyces grisoaurantiacus ATCC 19840

| Test Condition | A-39912 | ATCC 17755 S. (chainia) rubra | ATCC 23919 S. griseoruber | ATCC 19840 S. griseoauraantiacus |
|---|---|---|---|---|
| Spore chain morphology | Spiralled | Spiralled | Spiralled | Spiralled |
| Spore surface | Smooth | Smooth | Smooth | Smooth |
| Vegetative color | Purplish red to black; Reddish brown | Yellow brown Brownish orange | Yellow brown Reddish orange | Yellow brown Olive gray-Reddish brown |
| Aerial mass color | Red to gray | Red | Gray | Gray |
| Gelatin liquifaction | + | + | − | ± |
| Nitrate reduction | + | − | + | + |
| Skim milk | Peptonized | Hydrolyzed | Peptonized | Peptonized |
| Melanoid-like pigment production | − | − | − | − |
| Crystal[1] formation on: | | | | |
| ISP Med. #2 | + | − | − | − |
| ISP Med. #3 | + | − | − | − |
| Tomato Paste Oatmeal | + | − | − | − |
| Isomer of 2,6-diamino-pimelic acid | LL | LL | LL | LL |

[1] Crystals of undecylprodiginine

A number of the morphological and physiological properties of these four strains are in agreement, except for the vegetative color, aerial mass color, and granule formation on different media, as shown in Table V.

The narasin-producing Streptomyces granuloruber organism has been deposited and made a part of the stock culture collection of the Northern Regional Research Center, U.S. Department of Agriculture, Agricultural Research Service, Peoria, Ill., 61604, from which it is available to the public under the number NRRL 12389.

As is the case with other organisms, the characteristics of the narasin-producing culture Streptomyces granuloruber, NRRL 12389 are subject to variation. For example, mutants (spontaneous or induced), transconjugants and recombinants (including recombinant DNA on plasmids) of the NRRL 12389 strain, or derived from this strain, which produce the narasin antibiotic may be used in this invention.

A number of different media may be used to produce narasin with Streptomyces granuloruber, NRRL 12389. These media should contain assimilable sources of carbon, nitrogen, and inorganic salts. Suitable carbon sources include glucose, starch, and dextrin. Suitable nitrogen sources include peptone, enzymehydrolyzed casein, cottonseed meal, and meat peptone.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of narasin employing NRRL 12389, submerged aerobic fermentation in tanks is utilized. However, small amounts of narasin may be obtained by shake-flask culture. For tank fermentation, it is preferable to use a vegetative inoculum. The vegetative inoculum is prepared by inoculating a small volume of culture medium with the spore form, mycelial fragments, or a lyophylized pellet of the organism to obtain a fresh, actively growing culture of the organism. The vegetative inoculum is then transferred to a larger tank where, after a suitable incubation time, the narasin antibiotic is produced in optimal yield.

The pH of the uninoculated fermentation medium varies with the medium used for production, but the pH of all of the fermentation media falls in the range of from about pH 6.5 to about 7.5.

This narasin-producing organism can be grown over a broad temperature range of from about 25° to about 43° C. Optimum production of narasin with NRRL 12389 appears to occur at a temperature of about 30° C.

As is customary in aerobic submerged culture processes, sterile air is dispersed through the culture medium. For efficient growth of the organism, the volume of the air used in tank production is in the range of from about 0.25 to about 1.0 volume of air per volume of culture medium per minute (v/v/m). An optimum rate in a 10-liter vessel is about 0.2 v/v/m with agitation provided by conventional impellers rotating at about 400 RPM. It may be necessary to add small amounts (i.e., 0.2 ml/L.) of an antifoam agent such as propylene glycol to large-scale fermentation media if foaming becomes a problem.

Production of the narasin antibiotic can be monitored during the fermentation by either agar diffusion or turbidimetric methods. Test organisms suitable for use include *Staphylococcus aureus*, *Bacillus subtilis*, and *Micrococcus luteus*.

Antibiotic activity is generally present after about 40 hours and remains present for at least 2 or more days during the fermentation period. Peak antibiotic production occurs in from about 2 to about 4 days fermentation time.

The narasin antibiotic can be recovered from the fermentation medium by methods known in the art and described by Berg et al. in U.S. Pat. No. 4,038,384.

The novel narasin-producing organism *Streptomyces granuloruber*, NRRL 12389, produces substantial amounts of narasin factor A, as well as slight amounts of narasin factors B and D. The components may, as desired, be obtained as single antibiotics by further purification of the complex, for example by column chromatographic techniques. These factors are described in U.S. Pat. No. 4,038,384, which disclosure is hereby incorporated into and made a part of this application.

In order to illustrate more fully the operation of this invention, using varying fermentation media, the following Examples are provided. However, the scope of the invention is not intended to be limited thereby.

EXAMPLES

Example 1

The following medium was prepared for use in the agar slant culture of *Streptomyces granuloruber*, NRRL 12389:

| Ingredient | Amount (g/L.) |
| --- | --- |
| Potato dextrin | 10.0 |
| Enzyme-hydrolyzed casein[1] | 2.0 |
| Beef extract | 1.0 |
| Yeast extract | 1.0 |
| Agar | 2.0 |
| Czapek's mineral stock[2] | 2.0 ml/L. |
| Deionized water | q.s. to 1.0 liter |

[1]N—Z—Amine A (Humko Sheffield Chemical Co., Memphis, Tenn.)
[2]Czapek's mineral stock is prepared with the following ingredients:

| Ingredient | Amount (g/100 ml) |
| --- | --- |
| KCl | 10.0 |
| MgSO$_4$.7H$_2$O | 10.0 |
| FeSO$_4$.7H$_2$O | 0.2 |
| Deionized water | q.s. to 100 ml. |

Spores of *Streptomyces granuloruber*, NRRL 12389, were inoculated on a nutrient agar slant made up of the above-identified ingredients, and the thus-inoculated slant was incubated for about 7 days at a temperature of about 30° C. The mature slant culture was then covered with water and scraped with a sterile tool to loosen the spores and mycelium. One milliter of the resulting spore suspension was used to inoculate 100 ml. of vegetative medium of the following composition:

| Ingredient | Amount (g/L.) |
| --- | --- |
| Dextrose | 15.0 |
| Soybean meal | 15.0 |
| Corn steep liquor | 5.0 |
| CaCO$_3$ | 2.0 |
| NaCl | 5.0 |
| Czapek's mineral stock | 2.0 ml/L. |
| Deionized water | q.s. to 1.0 liter |

The vegetative inoculum was incubated in a 500 ml. wide-mouth Erlenmeyer flask at about 30° C. for about 48 hours on a reciprocal shaker with a two inch stroke at 108 SPM. This incubated medium is used either to inoculate small fermenters (the inoculum being approximately 1% per volume of fermenter medium) or to inoculate second stage flasks for the production of a larger volume of mycelium.

Two hundred milliter aliquots of the production medium were placed in 1.0 liter Erlenmeyer flasks and were sterilized at 121° C. for about 30 minutes. The production medium had the following composition:

| Ingredient | Amount (g/L.) |
| --- | --- |
| Dextrose | 10.0 |
| Edible molasses | 20.0 |
| Bacto Peptone | 5.0 |
| CaCO$_3$ | 2.0 |
| Czapek's mineral stock | 2.0 ml./L. |
| Deionized water | q.s. to 1.0 liter |

When cooled, the flasks were inoculated with a 5% inoculum of the vegetative inoculum. The culture was incubated on a reciprocal shaker at 108 SPM with a two-inch stroke. The pH of the fermentation at the end of 72 hours was about 7.5. The fermentation was run at 30° C.

EXAMPLE 2

Narasin was produced using a sterile production medium having the following composition:

| Ingredient | Amount (g/L.) |
| --- | --- |
| Silicone antifoam agent[1] | 0.2 |
| Glucose | 10.0 |
| Molasses | 20.0 |
| Peptone (Difco) | 5.0 |
| CaCO$_3$ | 2.0 |
| Deionized water | q.s. to 9.0 liters |

[1]Dow-Corning Antifoam A

This production medium, having a pH of 6.8, was sterilized for about 30 minutes at about 121° C. at 16 to 18 psi. The sterilized medium had a pH of 6.9. The sterilized medium was inoculated with 2.0% inoculum from the second-stage medium obtained as described in Example 1. The inoculated production medium was allowed to ferment in a 10-liter fermentation tank for about 3 days at a temperature of about 30° C. The fermentation medium was aerated with sterile air at the rate of 0.2 v/v/m and was stirred with conventional agitators at about 400 RPM.

EXAMPLE 3

Isolation and Purification

Eighteen liters of fermentation broth were adjusted to pH 3 with 1 N aqueous sulfuric acid and stirred for about one hour. The broth was filtered using filter aid (Hyflo Supercel filter aid, a diatomaceous earth produced by Johns-Manville Corporation), and the filter cake was washed with water. The filter cake was extracted with 9 l. of methanol containing 3 percent potassium acid carbonate by stirring for about one hour and filtering. The filter cake was then reextracted with 9 l. of methanol. The methanol extracts were combined and concentrated to a volume of about 2 l. and the pH adjusted to pH 7.5 with 1 N aqueous sulfuric acid. The mixture was extracted twice with 2 l. portions of ethyl acetate. The extracts were combined and concentrated in vacuo to a residue which was dissolved in 150 ml. of acetone. One hundred fifty ml. of water was added to the acetone solution and the pH was adjusted to pH 3.0 using 1 N aqueous hydrochloric acid. The mixture was stirred for about one hour. The oily crystals which formed were filtered and dissolved in 150 ml. of acetone and 150 ml. of water were added. The solution was held at room temperature overnight and the crystals which formed were filtered, washed with water, and dried in vacuo to yield crystals bearing an oily film.

The oily crystals were dissolved in 5 ml. of benzene and applied to a silica gel column (1.8×40 cm.—Grace Grade 62 silica gel) set in benzene. The column was washed successively with 250 ml. volumes of benzene, benzene:ethyl acetate (9:1), (4:1), (7:3), (1:1), and ethyl acetate, collecting fractions having volumes of 20–25 ml. The elution of activity was monitored by bioassay and also by thin-layer chromatography, which TLC employed silica gel plates with ethyl acetate as the developing solvent. Vanillin-sulfuric acid spray was used to detect the spots and *Bacillus subtilis* was used as the detection organism. The fractions containing only one component, identified as narasin, were combined and concentrated to dryness in vacuo. The residue was dissolved in 50 ml. of acetone, 50 ml. of water were added, and the solution was allowed to stand at room temperature for crystallization to occur. The crystals which formed were filtered and dried in vacuo to yield 172 mg. of white crystals having a melting point of about 75°–78° C.

The crystals were shown to be identical to narasin by comparison of NMR, IR, UV, and mass spectra, and thin-layer and paper chromatographic data. The biological data—antimicrobial and anticoccidial—were identical to that of authentic narasin.

To identify the purplish-red crystals produced by A-39912, the procedure described in the following Example 4 was employed.

EXAMPLE 4

Undecylprodiginine—Production and Identification

Plastic chromatography plates, measuring 23 cm.×45 cm., with a 10 mm. high edge, and containing 250 ml. of tomato paste oatmeal agar, prepared according to the teachings of Pridham et al., *Antibiot. Ann.* 1956–1957, pp. 947–953, were inoculated with a 48-hour inoculum using tryptone yeast broth, employing the cross-hatch method of Shirling and Gottlieb, supra. The tryptone yeast broth had the following composition:

| Ingredient | Amount (g/L.) |
| --- | --- |
| Tryptone (Difco) | 5.0 |
| Yeast extract | 3.0 |
| Distilled water | q.s. to 1.0 liter |

The broth measured pH 7.0–7.2 before being autoclaved before use. After inoculation, the plates were incubated 14 days at a temperature of 30° C., at which time purplish-red crystals were observed in the agar.

The agar containing the purplish-red crystals was cut out along the periphery of the culture growth, and extracted four times with 500 ml. of a mixture of chloroform:methanol (4:1) by stirring for 15 minutes over a steam bath. The extracts were combined and concentrated to dryness in vacuo. The residue was dissolved in 12 ml. of chloroform and chromatographed on a silica gel (Grace 62) column (1.2×52 cm.) packed in chloroform. The column was eluted with chloroform, collecting 10 ml. fractions. At fraction 34, the eluting solvent was changed to chloroform:methanol (95:5). The eluted fractions were monitored by thin-layer chromatography on silica-gel plates using chloroform:methanol (9:1) and observing the purple pigmented spots. Fractions 9–14, which contained the most intense purple color (single spot by TLC), were combined and concentrated to dryness. The residue was dissolved in dioxane and lyophilized, and a yield of 10.3 mg. of a purple powder was obtained. The purple powder gave a molecular mass ion of 393.27764 by high resolution election impact mass spectrometry, and an empirical formula of $C_{25}H_{35}N_3O$ by peak matching. This data, along with a comparison with the ultraviolet, infrared, and NMR spectra of undecylprodiginine, as reported in *Agr. Biol. Chem.* 31, 481 (1967), and *J. Antibiot.* 28, 194 (1975), served to identify the purple powder as undecylprodiginine.

I claim:

1. The method of producing the antibiotic narasin which comprises cultivating *Streptomyces granuloruber*, NRRL 12389, or a narasin-producing mutant or variant thereof, in a culture medium containing assimilable sources of carbohydrate, nitrogen, and inorganic salts under submerged aerobic fermentation conditions until a substantial amount of antibiotic activity is produced by said organism in said culture medium.

2. The method of claim 1 wherein the organism is *Streptomyces granuloruber*, NRRL 12389.

3. The method of claims 1 or 2 which includes the additional step of separating narasin from the culture medium.

4. A biologically pure culture of the microorganism *Streptomyces granuloruber*, NRRL 12389.

* * * * *